United States Patent [19]

Fujikura et al.

[11] Patent Number: 4,843,085
[45] Date of Patent: Jun. 27, 1989

[54] PYRIDINE DERIVATIVES, PROCESS FOR PRODUCTION THEREOF AND PHARMACEUTICAL COMPOSITIONS USEFUL AS ANTI-ARHYTMICS

[75] Inventors: Takashi Fujikura; Yuzo Matsumoto, both of Saitama; Masharu Asano, Tokyo, all of Japan

[73] Assignee: Yamanouchi Pharmaceutical Co., Ltd., Tokyo, Japan

[21] Appl. No.: 212,929

[22] Filed: Jun. 29, 1988

[30] Foreign Application Priority Data

Jul. 1, 1987 [JP] Japan .............................. 62-165746
Dec. 15, 1987 [JP] Japan .............................. 62-318076

[51] Int. Cl.$^4$ .................... C07D 213/70; A61K 31/44
[52] U.S. Cl. ..................................... 514/356; 546/321
[58] Field of Search ................. 514/356; 546/318, 321

[56] References Cited

U.S. PATENT DOCUMENTS 4,705,794 11/1987 Wehinger et al. .............. 514/356 X
4,727,082 2/1988 Fujikura et al. ..................... 514/356

Primary Examiner—Mary C. Lee
Assistant Examiner—E. Brendan Magrab
Attorney, Agent, or Firm—Burgess, Ryan & Wayne

[57] ABSTRACT

The present invention provides pyridine derivatives of following general formula (I) or a physiologically acceptable acid addition salt thereof:

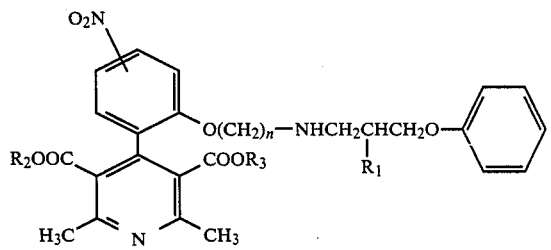

wherein $R_1$ is a hydrogen atom or a hydroxy group, $R_2$ and $R_3$, which may be the same or different, each is a lower alkyl group, and n is an integer of 1 to 6. The invention also provides for producing the pyridine derivative and pharmaceutical compositions containing the same. The compounds (I) possess anti-arrhythmic activity.

16 Claims, No Drawings

PYRIDINE DERIVATIVES, PROCESS FOR PRODUCTION THEREOF AND PHARMACEUTICAL COMPOSITIONS USEFUL AS ANTI-ARHYTMICS

FIELD OF THE INVENTION

The present invention relates to novel pyridine derivatives. In one aspect, the invention is directed to certain novel pyridine derivatives which exhibit anti-arthythmic activity. In a further aspect, the invention relates to methods of preparing the derivatives, pharmaceutical compositions containing such derivatives and methods of use.

SUMMARY OF THE INVENTION

In its brood respect, the present invention is directed to pyridine derivatives represented by the following formula (I) and also includes physiologically acceptable acid addition salts thereof:

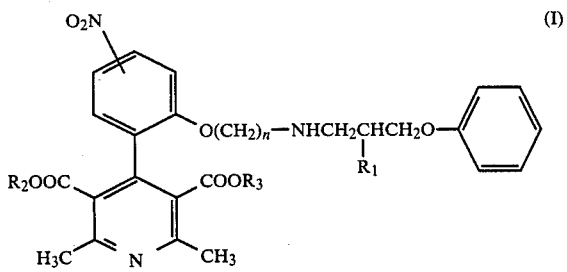

(I)

wherein $R_1$ represents a hydrogen atom or a hydroxy group, $R_2$ and $R_3$, which may be the same or different, each represents a lower alkyl group and n represents an integer of 1 to 6. The present invention further provides a process for preparing the pyridine derivatives represented by general formula (I) or the physiologically acceptable acid addition salts thereof. The present invention also relates to pharmaceutical compositions containing the above pyridine derivatives or a salt thereof, as at least one active ingredient, and a pharmaceutically acceptable carrier or excipient.

The desired compounds of the present invention are novel and characterized in that the 2-substituted nitrophenyl group binds to a di-lower alkyl 2,6-dimethylpyridine-3,5-dicarboxylate.

DETAILED DESCRIPTION OF THE INVENTION

The compounds included in the above general formula (I) can be illustrated in more detail as follows:

In the definitions of the substituents used in the general formula (I), the term "lower alkyl group" means a straight or branched carbon chain containing 1 to 6 carbon atoms. More particularly, the "lower alkyl group" means a straight or branched carbon chain containing 1 to 6 carbon atoms. More particularly, the "lower alkyl group" includes, among others, methyl, ethyl, propyl, butyl, pentyl, hexyl, sec-butyl, tert-butyl and neo-pentyl groups.

Some compounds of the present invention contain one or more asymmetric carbon atoms and hence stereoisomers. The compounds of general formula (I) include all of the isomers individually and in any mixture such as a racemic compound, an optically active isomer and a diastereoisomer.

The compounds of general formula (I) can form pharmacologically acceptable acid addition salts. Representative examples of such salts are inorganic acid addition salts such as hydrochloride, hydrobromide, hydroiodide, sulfate, nitrate, phosphate, etc. and organic acid addition salts such as methanesulfonate, ethanesulfonate, oxalate, maleate, fumarate, etc.

The compounds of formula (I) of the present invention can be produced utilizing various synthetic methods. Typical examples of applicable processes are given below.

Process 1

The compounds of formula (I) of the present invention can be produced by a process as shown by the following reaction scheme:

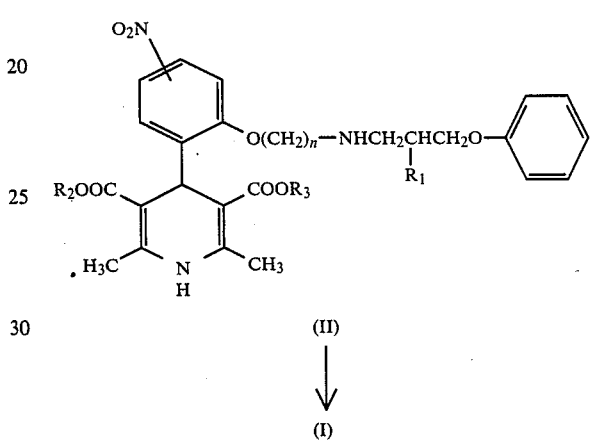

wherein $R_1$ represents a hydrogen atom or a hydroxy group, $R_2$ and $R_3$, which may be the same or different, each represents a lower alkyl group and n represents an integer of 1 to 6.

The pyridine derivatives (I) of the present invention can be prepared by oxidizing a corresponding dihydropyridine derivative (II). The starting compounds, dihydropyridine derivatives (II), can be produced, for example, by a process described in EP-A-0 167 371.

Oxidation can be performed by reacting the dihydropyridine derivatives in dioxane, acetic acid or water or a mixture thereof with an oxidizing agent. Examples of an oxidizing agent include nitric acid and nitrous acid (e.g. sodium nitrite—nitric acid, sodium nitrite—sulfuric acid or sodium nitrite—acetic acid). The reaction temperature is not critical, but the reaction is preferably carried out at about room temperature or with heating.

Process 2

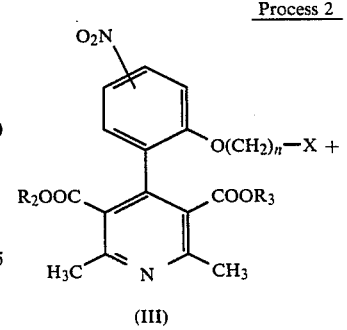

(III)

-continued
Process 2

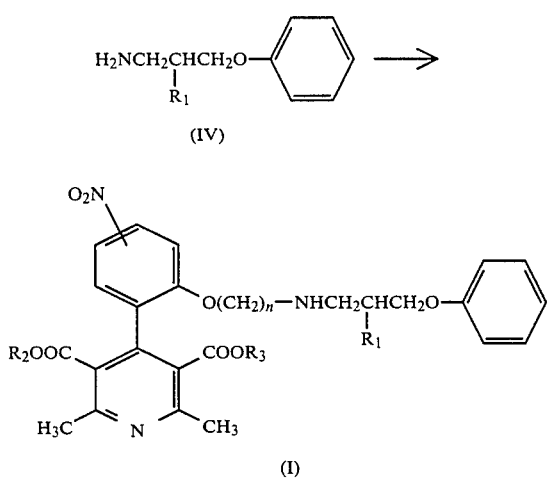

wherein X represents a halogen atom or a toluenesulfonyloxy group and $R_1$, $R_2$, $R$ and n have the same meaning as above-defined.

The compounds of formula (I) of the present invention also can be produced by reacting a halogenoalkoxy (or toluene-sulfonyloxyalkoxy)nitrophenyl-substituted pyridine derivative shown by formula (III) above with an amine derivative as shown by formula (IV) above.

Examples of the halogens include iodine, bromine, and chlorine. A representative example of the toluenesulfonyloxy group is a p-toluenesulfonyloxy group.

When using the starting compound (III) wherein the side chain thereof is substituted with a halogen atom, the reaction can be performed in the absence or presence of a solvent. Any solvents which do not adversely influence the reaction can be employed. Examples of these solvents include benzene, toluene, xylene, dimethylformamide, acetonitrile, dichloromethane, dichloroethane, methanol, ethanol and the like. The reaction can preferably be performed by reacting compound (III) with an equimolar or slightly excess molar amount of compound (IV) at about room temperature, with heating, or under reflux.

It may be preferred for a smooth reaction to operate in the presence of a base. Examples of suitable bases are secondary or tertiary organic amines such as pyridine, picoline, N,N-dimethylaniline, N-methylmorpholine, trimethylamine, triethylamine, dimethylamine, and inorganic bases such as potassium carbonate, sodium carbonate, sodium bicarbonate and the like.

In order to avoid possible side-reactions, one may protect the amino group of the compound (IV) and then react the amino protected compound with compound (III), and release the protective group after completion of the reaction. Examples of protective groups for the amino group include phenyl-substituted methyl groups such as e.g. benzyl, p-methoxybenzyl, trityl and the like, and unsubstituted or substituted silyl groups and the like. The release of the protective groups can be easily effected in a conventional manner.

When using starting compounds (III) wherein the side chain thereof is substituted with a toluenesulfonyl group, an equimolar or slightly excess amount of the compound (IV) is preferably reacted with compound (III) in an inert solvent such as ether, methanol, ethanol, toluene, tetrahydrofuran and the like, under cooling or at about room temperature. The reaction time may vary according to reaction conditions.

Process 3

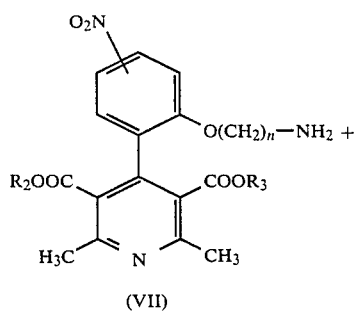

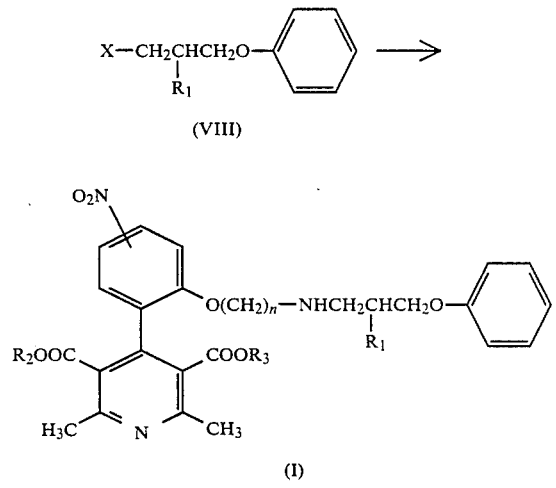

wherein X, $R_1$, $R_2$, $R_3$ and n have the same meaning as above.

The compound of formula (I) can be prepared by reacting a compound (VII) with a halide or tosylate compound as shown by general formula (VIII). The reaction conditions are approximately the same as in process 2.

Process 4

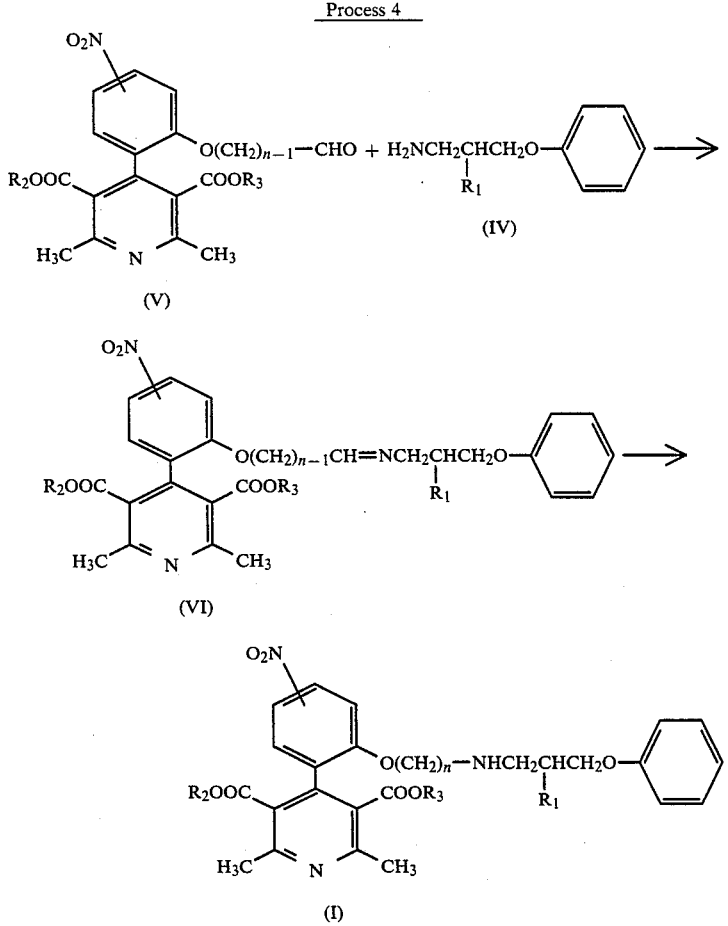

wherein $R_1$, $R_2$, $R_3$ and n have the same meaning as above.

The compound of formula (I) of the present invention can be prepared by reacting a pyridine derivative (V), which is substituted with a formylalkoxy (or formyloxy)-nitrophenyl groups at the 4-position, with an amine compound (IV) to give a Schiff base, and then reducing the Schiff base under conditions which do not reduce the nitro group in the compound. The reaction to produce the Schiff base can be performed in the absence of any solvent, but usually in the presence of an inert organic solvent such as alcohols, e.g. methanol, ethanol, etc. and benzene. The compound (V) is usually reacted with an equimolar or slightly excess amount of the compound (VI). The reaction can be performed at about room temperature, with heating, or under reflux. According to the reaction conditions, potassium hydroxide may be added to the reaction system, and/or it may be preferred to remove water formed during the reaction by using a Dean-Stark trap.

In the reducing step of the Schiff base, a reducing agent may be added to the reaction solution obtained in the preceeding step, without isolating the Schiff base formed.

In order to selectively reduce the imino group in the Schiff base to give the desired compound (I) without reducing the nitro group, it may be advantageous to employ boron compounds such as sodium borohydride, lithium borohydride, sodium borocyanohydride and the like.

The reduction can be carried out in an organic solvent such as an alcohol, e.g. methanol, ethanol and the like, and acetic acid or in water or in a mixture thereof. The reaction is usually performed at about room temperature or with heating.

For a smooth reaction, it may be preferred to operate while maintaining the reaction system at a neutral or basic state. If necessary, for example, methylamine, ethylamine, propylamine, dimethylamine, potassium hydroxide or sodium acetate may be added to the reaction system.

An individual isomer of the pyridine derivative (I) of the present invention can be prepared by resolving a racemate or diastereoisomer by using a conventional method or obtained by employing a suitable starting compound.

The desired compounds of formula (I) according to the present invention can be isolated as free bases or the desired salts and then purified. Isolation and purification are performed by using conventional techniques such as extraction, crystallization, recrystallization, various kinds of chromatography and the like.

The compounds of formula (I) of this invention possess an inhibiting effect in warm blooded animals including humans against aconitine-induced arrhythmia, whereas the same compounds had almost no calcium antagonistic and beta-adrenoceptor blocking effects Some compounds (I) also have local anesthetic activity.

The inhibiting effect against aconitine-induced arrhythmia of the compounds (I) of this invention is shown in the following test results employing the indicated test method.

The results demonstrated that the desired compounds (I) produce anti-arrhythmic activity at doses of about 0.1 to 10 mg/kg in intravenous administration to rats, and at doses of about 10 to 100 mg/kg in oral administration to rats.

(1) Inhibiting effect against aconitine-induced arrhythmia

The inhibiting effect against aconitine-induced arrhythmia was evaluated according to the method of Hass and Busch (Arzneimittel Forschung, 18, 401–407, 1968) using rats (Wistar strain, male weighing 260–370 g) anesthetized with urethane. Pretreatment of intravenous or oral administration of the compounds (I) was performed and 5 min. later followed by aconitine-intravenous infusion (2.5 g/0.103 ml/min). The mean doses of aconitine at which the first ectopic beat appeared in ECG was then determined. Anti-arrhythmic potency was evaluated by calculating the dose required to increase the mean dose of aconitine by 50% ($ED_{50}$ value, mg/kg i.v. and p.o.). The results are shown in Table 1.

TABLE 1

Anti-arrhythmic activities of the compounds (I) of this invention, propafenone and disopyramide.

| Compound | $ED_{50}$ (mg/kg i.v.) | $ED_{50}$ (mg/kg p.o.) |
|---|---|---|
| Compound of Example 1 | 1.67 | 25 |
| Compound of Example 2 | 2.59 | 18 |
| Compound of Example 3 | 0.81 | 27 |
| Propafenone | 2.77 | 118 |
| Disopyramide | 7.19 | 36 |

The local anesthetic activity of the compounds (I) is shown in the following test results employing the indicated test methods.

(2) Local anesthetic activity

Local anesthetic activity of the compounds (I) of this invention was determined according to the method of Chance and Lobstein (Journal of Pharmacology and Experimental Therapeutics, 82, 203–210, 1944) using male Hartley strain guinea-pigs weighing 300 to 450 g. Solutions of the compounds were instilled into the cornea, and the corneal reflex responses were determined. The local anesthetic potency was evaluated by calculating the concentration required to inhibit corneal reflex responses by 50% ($ED_{50}$, %). The results are shown in Table 2.

TABLE 2

Local anesthetic activity of the compound of this invention and lidocaine.

| Compound | $ED_{50}$ (%) |
|---|---|
| Compound of Example 1 | 0.49 |
| Compound of Example 2 | 0.32 |
| Lidocaine | 0.82 |

The pharmaceutical composition containing one or more of the compounds shown by general formula (I) or salts thereof as active ingredients are prepared using conventional pharmaceutical carriers or excipients and are formulated to form tablets, powder, parvules, granules, capsules, pills, solution, injection, suppository, ointment, adhesive and the like. The medicaments are administered orally (including sublingual administration) or parenterally wherein the therapeutically active material is found in amounts varying between about 0.015 and about 10 mg/kg of body weight of the subject.

The appropriate clinical dose of the compounds of formula (I) is determined considering factors such as the symptoms, weight, age and sex of patients. For an adult a daily dose of 1 to 200 mg or 100 to 600 mg is usually administered intravenously or orally, respectively, in one to several individual doses.

The following Examples are further illustrative of the present invention. The production of the starting compounds are described in the Reference Examples.

REFERENCE EXAMPLE 1

Dimethyl 2,6-dimethyl-4-[(4-bromobutoxy)-5-nitrophenyl]pyridine-3,5-dicarboxylate

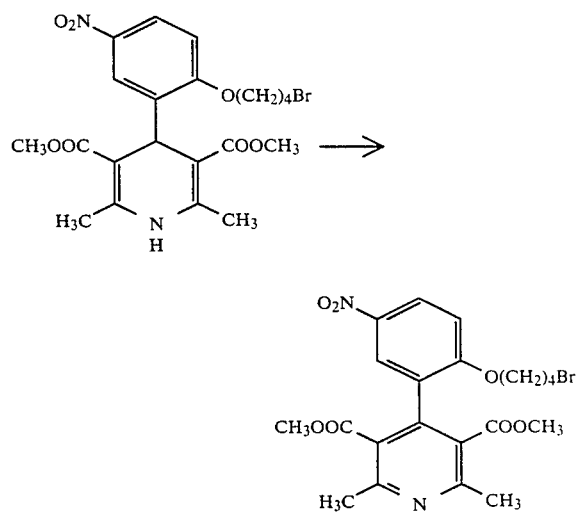

To 140 ml of 50% dioxane-water solution was added 12.8 ml conc. nitric acid (d=1.40), and suspended therein 20 g of dimethyl 4[(4-bromobutoxy)-5-nitrophenyl]-2,6-dimethyl-1,4-dihydropyridine-3,5-dicarboxylate while maintaining the system at 5° to 10° C. under ice cooling. After adding 5.6 g of sodium nitrite, the reaction mixture was vigorously stirred and then filtered. The filtrate obtained was adjusted to pH8 with a saturated aqueous solution of sodium bicarbonate and extracted with chloroform. After washing with water, the organic layer was dried over anhydrous magnesium sulfate and the solvent distilled off. The resultant residue was recrystallized from ethyl acetate—ether to yield 10.4 g of dimethyl 2,6-dimethyl-4-[(4-bromobutoxy)-5-nitrophenyl]pyridine-3,5-dicarboxylate.

(i) Melting point: 142°–144° C.

(ii) Nuclear magnetic resonance spectrum (CDCl) δ (ppm): 1.7–2.0 (4H,m), 2.68 (6H,s) 3.2–4.0 (2H,m), 3.62 (6H,s) 3.9–4.2 (2H,m), 6.9–7.0 (1H,m) 8.0–8.05 (1H,m), 8.2–8.4 (1H,m)

The following compounds of Reference Examples 2–6 were obtained in the same manner as in Reference Example 1:

REFERENCE EXAMPLE 2

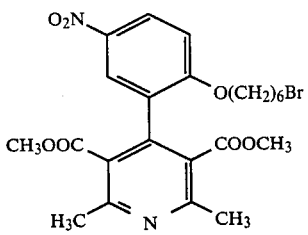

(i) Melting point: 99°–101° C.
(ii) Nuclear magnetic resonance spectrum (CDCl$_3$) δ (ppm): 1.2–1.9 (8H,m), 2.65 (6H,s) 3.3–3.4 (2H,m), 3.57 (6H,s) 3.9–4.1 (2H,m), 6.9 (1H,d) 8.1 (1H,d), 8.3 (1H,dd)
(iii) Mass spectrum: 522, 524

REFERENCE EXAMPLE 3

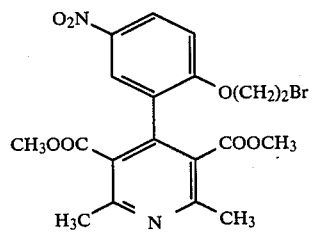

(i) Amorphous powder
(ii) Nuclear magnetic resonance spectruc (CDCl$_3$) δ (ppm): 2.65 (6H,s), 3.4–3.6 (8H,m) 4.2–4.4 (2H,m), 7.0 (1H,d) 8.1 (1H,d), 8.3 (1H,dd)
(iii) Mass spectrum: 466, 468

REFERENCE EXAMPLE 4

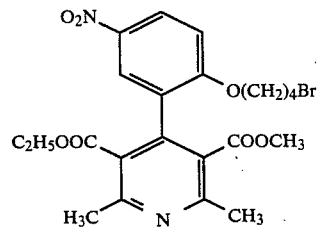

(i) Melting point: 115°–117° C.
(ii) Nuclear magnetic resonance spectrum (CDCl$_3$) (ppm) 1.0 (3H,t), 1.7–2.0 (4H,m) 2.64 (6H,s), 3.2–3.4 (2H,m) 3.56 (3H,s), 3.9–4.2 (4H,m) 7.0 (1H,d), 8.0 (1H,d) 8 3 (1H,dd)
(iii) Mass spectrum: 508, 510

REFERENCE EXAMPLE 5

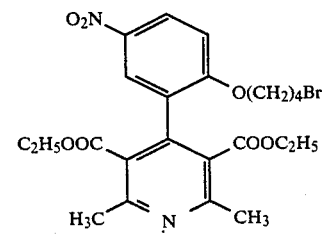

(i) Amorphous powder
(ii) Nuclear magnetic resonance spectrum (CDCl$_3$) (ppm): 1.0 (6H,t), 1.7–1.9 (4H,m) 2.64 (6H,s), 3.2–3.4 (2H,m) 3.9–4.2 (6H,m), 6.9 (1H,d) 8.1 (1H,d), 8.3 (1H,dd)
(iii) Mass spectrum FAB (Pos.): 523, 525 (M+1)

REFERENCE EXAMPLE 6

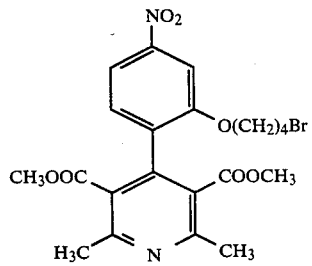

(i) Oily
(ii) Nuclear magnetic resonance spectrum (CDCl$_3$) δ (ppm): 1.7–1.9 (4H,m), 2.63 (6H,s) 3.2–3.4 (2H,m), 3.54 (6H,s) 3.9–4.1 (2H,m), 7.2 (1H,d) 7.8 (1H,d), 7.9 (1H,dd)
(iii) Mass spectrum: 494, 496

EXAMPLE 1

Dimethyl 4-[2-[4-[[(S)-2-hydroxy-3-phenoxypropyl]amino]butoxy]-5-nitrophenyl]-2,6-dimethylpyridine-3,5dicarboxylate dioxalate In 100 ml of 2N nitric acid under vigorously stirring was suspended 10 g of dimethyl 4-[2-[4-[[(S)-2-hydroxy-3phenoxypropyl]amino]butoxy]-5-nitrophenyl]-2,6-dimethyl-1,4-dihydropyridine-3,5-dicarboxylate and the suspension heated at 80° C. for one hour. After cooling, the reaction mixture was made alkaline with a 10% sodium hydroxide aqueous solution and extracted with chloroform. The extract was dried over anhydrous magnesium sulfate and the solvent distilled off under reduced pressure. The resultant residue was subjected to silica gel column chromatography and eluted with chloroform - methanol (98:2) to give 4.8 g of oily dimethyl 4-[2-[4-[[(S)-2-hydroxy-3-phenoxypropyl]amino] butoxy]-5-nitrophenyl]-2,6-dimethylpyridine-3,5-dicarboxylate (i) Nuclear magnetic resonance spectrum (CDCl$_3$) (ppm): 1.6–2.1 (4H,bs), 2.62 (6H,s) 2.7–3.3 (4H,m), 3.56 (6H,s) 3.8–4.2 (4H,m), 4.4–4.7 (1H,m) 4.8–5.6 (3H,m; exchange with D$_2$O) 6.8–7.1 (3H,m), 7.1–7.4 (3H,m) 8.02 (1H,m), 8.1–8.3 (1H,m)
(ii) Mass spectrum FAB (Pos.): 582 (M+)

The above compound was dissolved in 15 ml of ethanol, and after dissolving 1.5 g of oxalic acid with heating, the resultant solution was allowed to stand overnight at 4° C. The precipitated crystals were collected by filtration and recrystallized from ethanol to give 1.5 g of dimethyl 4-[2-[4- (S)-2-hydroxy-3-phenoxypropyl]amino]butoxy]-5-nitrophenyl]-2,6-dimethyl-pyridine-3,5-dicarboxylate dioxalate. This compound has the following physico-chemical properties:
(i) Melting point: 159°–161° C.
(ii) Elemental analysis (for C$_{34}$H$_{39}$N$_3$O$_{17}$)

|  | C (%) | H (%) | N (%) |
| --- | --- | --- | --- |
| Calc. | 53.61 | 5.16 | 5.52 |
| Found | 53.54 | 5.15 | 5.57 |

(iii) Nuclear magnetic resonance spectrum (DMSO-$d_6$)

(ppm): 1.5–1.9 (4H,bs), 2.6 (6H,s) 2.7–3.1 (4H,m), 3.56 (6H,s) 3.9–4.2 (5H,), 6.9–7.1 (3H,m) 7.2–7.4 (3H,m), 7.9 (1H,m) 8.3–8.4 (1H,m)

EXAMPLE 2

Dimethyl 4-[2-[4-[[(R)-2-hydroxy-3-phenoxypropyl]amino]butoxy]-5-nitrophenyl]-2,6-dimethylpyridine-3,5-dicarboxylate oxalate Ten g of dimethyl 4-[2-[4-[[(R)-2-hydroxy-3-phenoxypropyl]amino]butoxy]-5-nitrophenyl-2,6-dimethyl-1,4-dihydrpyridine-3,5-dicarboxylate was treated in the same manner as in Example 1 to give 4.2 g of oily dimethyl 4-[2-[4-[[(R)-2-hydroxy-3-phenoxypropyl]amino]butoxy]-5-nitrophenyl]-2,6-dimethylpyridine-3,5-dicarboxylate. In 35 ml of ethanol was dissolved the compound obtained as above and dissolved 0.7 g of oxalic acid with heating. The resultant solution was allowed to stand overnight at 4° C. The precipitated crystals were collected by filtration and recrystallized from ethanol (30 ml) to yield 2.7 g of dimethyl 4-[2-[4-[[(R)-2-hydroxy-3-phenoxypropyl]amino]butoxy]-5-nitrophenyl]-2,6-dimethyl pyridine-3,5-dicarboxylate oxalate. This compound has the following physico-chemical properties:

(i) Melting point: 134°–135° C.

(ii) Elemental analysis (for $C_{32}H_{37}N_3O_{13}$)

|  | C (%) | H (%) | N (%) |
| --- | --- | --- | --- |
| Calc. | 57.22 | 5.55 | 6.26 |
| Found | 57.28 | 5.49 | 6.10 |

(iii) Nuclear magnetic resonance spectrum (DMSO-$d_6$)

(ppm) 1.5–1.9 (4H,bs), 2.52 (6H,s) 2.7–3.1 (4H,m), 3.52 (6H,s) 3.8–4.4 (5H,m), 6.8–7.1 (3H,m) 7.2–7.4 (3H,m), 7.9 (1H,m) 8.2–8.4 (1H,m)

EXAMPLE 3

Dimethyl 2,6-dimethyl-4-[5-nitro-2-[4-[(3-phenoxypropyl) amino]butoxy]phenyl]pyridine-3,5-dicarboxylate oxalate

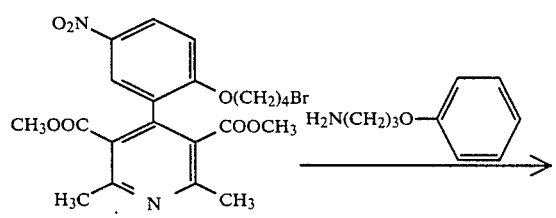

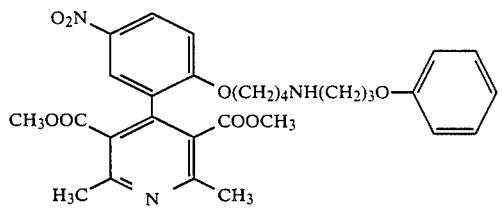

2.22 g of dimethyl 2,6-dimethyl-4-[(4-bromobutoxy)-5-nitro-phenyl]pyridine-3,5-dicarboxylate and 1.4 g of 3-phenoxypropylamine were dissolved in 30 ml of acetonitrile and refluxed with heating for two hours. After evaporating the solvent, the residue was subjected to silica gel column chromatography and eluted with chloroform - methanol (95:5) to give 1.8 g of caramel-like dimethyl 2,6-dimethyl-4-[5-nitro-2-[4-[(3-phenoxypropyl)amino]butoxy]phenyl]pyridine3,5-dicarboxylate. The compound thus obtained in 29 ml of ethanol was dissolved and to the solution was added a solution of 0.2 g of anhydrous oxalic acid in 5 ml of ethanol. The resultant solution was allowed to stand overnight at 4° C. The precipitated crystals were collected by filtration and recrystallized from ethanol to give 1.5 g of dimethyl 2,6-dimethyl-4-[5-nitro-2-[4-[(3-phenoxypropyl)amino]-butoxy]phenyl]pyridine-3,5-dicarboxylate oxalate. This compound has the following physico-chemical properties:

(i) Melting point 100°–101° C.

(ii) Elemental analysis (for $C_{32}H_{37}N_3O_{12}$)

|  | C (%) | H (%) | N (%) |
| --- | --- | --- | --- |
| Calc. | 58.62 | 5.69 | 6.41 |
| Found | 58.21 | 5.64 | 6.51 |

(iii) Nuclear magnetic resonance spectrum (DMSO-$d_6$)

(ppm): 1.4–1.8 (4H,bs), 1.9–2.2 (2H,m) 2.4–2.6 (8H,m), 2.7–3.2 (4H,m) 3.54 (6H,s), 3.9–4.2 (4H,m) 6.8–7.0 (3H,m), 7.2–7.4 (3H,m) 7.8–7.9 (1H,m), 8.2–8.4 (1H,m)

The following compounds of Examples 4 to 8 were obtained in the same manner as in Example 3.

EXAMPLE 4

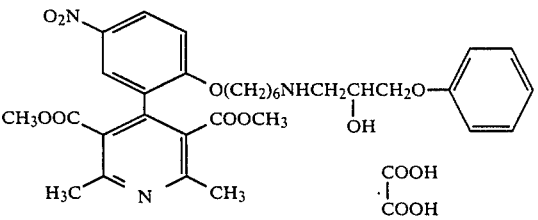

(i) Melting point 157°–159° C.

(ii) Elemental analysis (for $C_{34}H_{41}N_3O_{13}$)

|  | C (%) | H (%) | N (%) |
| --- | --- | --- | --- |
| Calc. | 58.36 | 5.91 | 6.01 |
| Found | 58.33 | 5.77 | 5.97 |

(iii) Nuclear magnetic resonance spectrum (DMSO-d$_6$)

(ppm): 1.1–1.7 (8H,m), 2.56 (6H,s) 2.7–3.2 (4H,m), 3.53 (6H,s) 3.9–4.3 (5H,m), 6.8–7.1 (3H,m) 7.2–7.4 (3H,m), 7.9 (1H,d) 8.4 (1H,dd)

(iv) Mass spectrum FAB (Pos.): 610 (M+1)

EXAMPLE 5

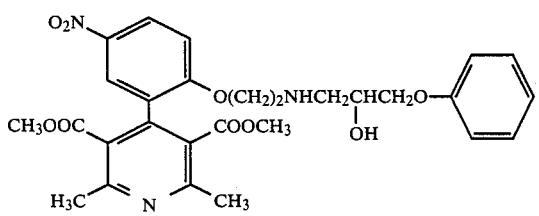

(i) Amorphous (ii) Elemental analysis (for C$_{28}$H$_{31}$N$_3$O$_9$ 0.5 H$_2$O)

|  | C (%) | H (%) | N (%) |
|---|---|---|---|
| Calc. | 59.78 | 5.73 | 7.47 |
| Found | 59.67 | 5.68 | 7.50 |

(iii) Nuclear magnetic resonance spectrum (CDCl$_3$)

(ppm): 2.63 (6H,s), 2.7–2.8 (2H,m) 2.9–3.0 (2H,m), 3.56 (6H,s) 3.9–4.0 (3H,m), 4.1–4.2 (2H,m) 6.9–7.1 (4H,m), 7.2–7.4 (2H,m) 8.1 (1H,d), 8.3 (1H,dd)

(iv) Mass spectrum FAB (Pos.): 554 (M+1)

EXAMPLE 6

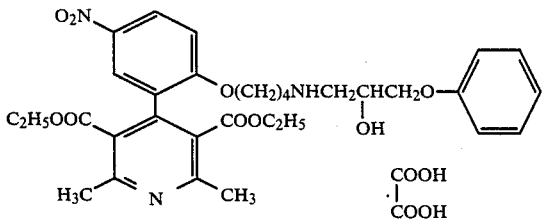

(i) Amorphous (ii) Elemental analysis (for C$_{34}$H$_{41}$N$_3$O$_{13}$ 0.7 H$_2$O)

|  | C (%) | H (%) | N (%) |
|---|---|---|---|
| Calc. | 57.33 | 6.00 | 5.90 |
| Found | 57.34 | 6.13 | 5.67 |

(iii) Nuclear magnetic resonance spectrum (DMSO-d$_6$)

δ(ppm): 0.9 (6H,t), 1.4–1.8 (4H,m) 2.54 (6H,s), 2.7–3.1 (4H,m) 3.8–4.2 (9H,m), 6.8–7.0 (3H,m) 7.2–7.4 (3H,m), 7.9 (1H,d) 8.4 (1H,dd)

(iv) Mass spectrum FAB (Pos.): 610 (M+1)

EXAMPLE 7

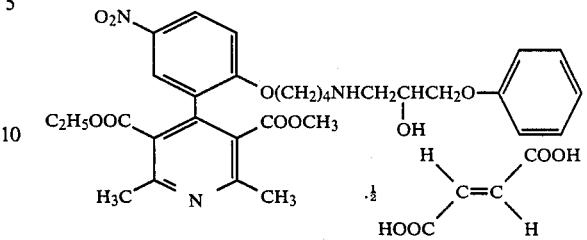

(i) Amorphous (ii) Elemental analysis

|  | C (%) | H (%) | N (%) |
|---|---|---|---|
| Calc. | 58.23 | 6.22 | 6.17 |
| Found | 58.26 | 6.04 | 6.13 |

(iii) Nuclear magnetic resonance spectrum (DMSO-d$_6$)

δ (ppm): 0.9 (3H,t), 1.4–1.8 (4H,m) 2.56 (6H,s), 2.6–2.9 (4H,m) 3.54 (3H,s), 3.9–4.2 (7H,m) 6.45 (H,s), 6.8–7.0 (3H,m) 7.2–7.4 (3H,m), 7.9 (1H,d) 8.3 (1H,dd)

(iv) Mass spectrum FAB (Pos.): 596 (M+1)

EXAMPLE 8

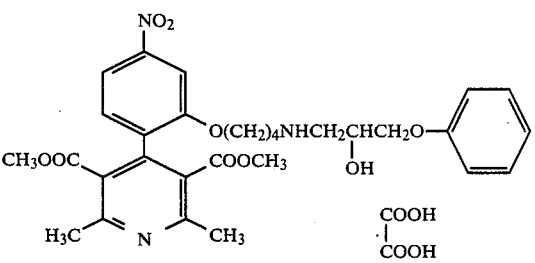

(i) Amorphous (ii) Elemental analysis (for C$_{32}$H$_{37}$N$_3$O$_{13}$ 0.4 H$_2$O)

|  | C (%) | H (%) | N (%) |
|---|---|---|---|
| Calc. | 56.62 | 5.61 | 6.19 |
| Found | 56.65 | 5.48 | 6.11 |

(iii) Nuclear magnetic resonance spectrum (DMSO-d$_6$)

δ (ppm): 1.5–1.9 (4H,m), 2.53 (6H,s) 2.7–3.1 (4H,m), 3.55 (6H,s) 3.8–4.3 (5H,m) 6.8–7.1 (3H,m) 7.2–7.4 (3H,m), 7.8–8.0 (2H,m)

(iv) Mass spectrum FAB (Pos.): 582 (M+1)

EXAMPLE 9

Dimethyl 2,6-dimethyl-4-[5-nitro-2-[4-[(3-phenoxypropyl) amino]butoxy]phenyl]pyridine-3,5-dicarboxylate oxalate

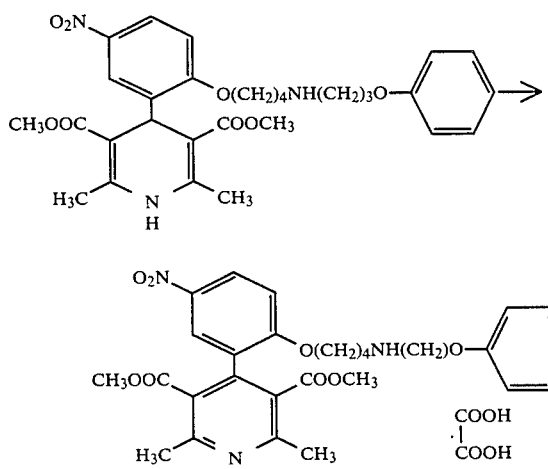

In 10 ml of 2N nitric acid there was suspended under vigorously stirring 1 g of dimethyl 2,6-dimethyl-4-[5-nitro2-[4-(3-phenoxypropylamino)butoxy]phenyl]-2,6-dimethyl-1,4-dihydropyridine-3,5-dicarboxylate and the suspension heated at 75° C. for one hour. After cooling, the suspension was made alkaline with 10 % sodium hydroxide aqueous solution and extracted with chloroform. After washing with water, the organic layer was dried over anhydrous magnesium sulfate and the solvent was distilled off. The resultant residue was subjected to silica gel column chromatography and eluted with chloroform - methanol (98:2) to give 0.21 g of caramel-like kimethyl 2,6-dimethyl-4-[5-nitro-2-[4-[(3-phenoxypropyl) amino]butoxy]phenyl]pyridine-3,5-dicarboxylate. In 3 ml of ethanol was dissolved the compound obtained as above and 0.034 g of anhydrous oxalic acid, and the solution allowed to stand overnight at 4° C. The precipitated crystals were collected by filtration and recrystallized from ethanol to give 0.18 g of dimethyl 2,6-dimethyl-4-[5-nitro-2-[4-[(3-phenoxypropyl] amino]butoxy]phenyl]pyridine-3,5-dicarboxylate oxalate. This compound has the same physicochemical properties as those of Example 3.

The following compounds of Examples 10 and 11 were obtained in the same manner as in Example 9.

Example 10

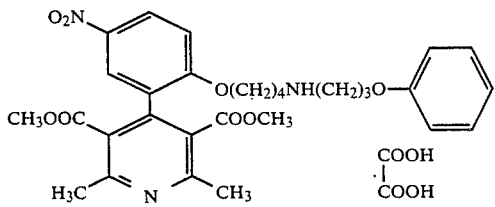

(i) Amorphous
(ii) Elemental analysis (for $C_{34}H_{41}N_3O_{12}H_2O$)

|  | C (%) | H (%) | N (%) |
|---|---|---|---|
| Calc. | 58.20 | 6.18 | 5.99 |
| Found | 58.02 | 5.95 | 5.89 |

(iii) Nuclear magnetic resonance spectrum (DMSO-$d_6$) δ (ppm): 1.1–1.8 (8H,m), 1.9–2.2 (2H,m) 2.54 (6H,s), 2.7–3.2 (4H,m) 3.51 (6H,s), 4.0–4.2 (4H,m) 6.8–7.0 (3H,m), 7.1–7.4 (3H,m) 7.9 (1H,d) 8.3 (1H,dd)

(iv) Mass spectrum FAB (Pos.): 594 (M+1)

EXAMPLE 11

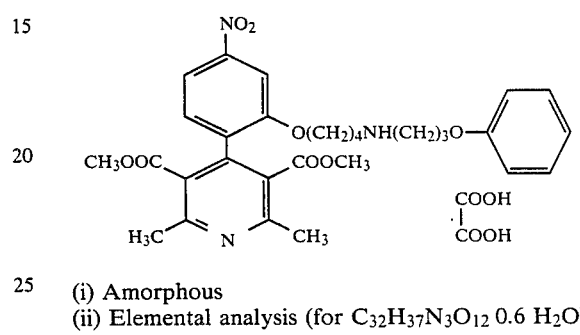

(i) Amorphous
(ii) Elemental analysis (for $C_{32}H_{37}N_3O_{12}$ 0.6 $H_2O$)

|  | C (%) | H (%) | N (%) |
|---|---|---|---|
| Calc. | 57.67 | 5.78 | 6.30 |
| Found | 57.73 | 5.79 | 6.16 |

(ii) Nuclear magnetic resonance spectrum (DMSO-$d_6$)

δ (ppm): 1.5–1.8 (4H,m), 1.9–2.2 (2H,m) 2.52 (6H,s), 2.7–3.1 (4H,m) 3.51 (6H,s), 3.9–4.2 (4H,m) 6.8–7.0 (3H,m), 7.2–7.4 (3H,m) 7.8–8.0 (2H,m)

(v) Mass spectrum FAB (Pos.): 566 (M+1)

EXAMPLE 12

| The compound of Example 1 | 100 g |
|---|---|
| Starch | 185 g |
| Lactose | 25 g |
| Magnesium stearate | 1.5 g |

The above ingredients were granulated using starch paste as a binding agent and the granules were compacted in a conventional manner to form 1,000 tablets of 100 mg per tablet.

What is claimed is:

1. A pyridine derivative represented by the following formula:

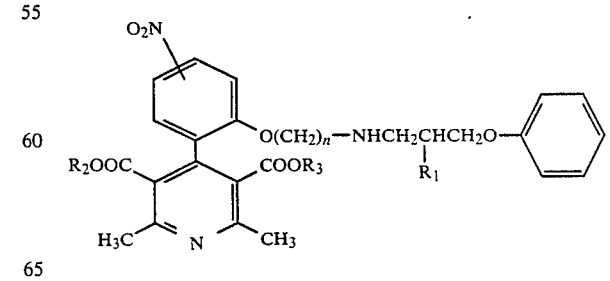

and the physiologically acceptable acid addition salts thereof, wherein $R_1$ represents a hydrogen atom or a hydroxy group, $R_2$ and $R_3$, which may be the same or different, each represents a lower alkyl group, and n represents an integer of 1 to 6.

2. A pyridine derivative or the physiologically acceptable acid addition salt thereof claimed in claim 1, wherein $R_1$ represents a hydroxy group, $R_2$ and $R_3$ represent a $C_1$-$C_3$ alkyl group and n represents an integer of 3 to 5.

3. A pyridine derivative or the physiologically acceptable acid addition salt thereof claimed in claim 2, wherein $R_2$ and $R_3$ represent a methyl group and n represents an integer of 4.

4. A pyridine derivative or the physiologically acceptable acid addition salt thereof claimed in claim 1, wherein $R_1$ represents a hydrogen atom.

5. A physiologically acceptable acid addition salt of the pyridine derivative claimed in claim 1 which is a salt of an organic acid.

6. A physiologically acceptable acid addition salt of the pyridine derivative claimed in claim 5 which is a salt of oxalic acid.

7. A pharmaceutical composition useful as an anti-arrythmic agent and comprised of at least one anti-arrythmic effective amount of the pyridine derivative of claim 1 and a pharmaceutically acceptable carrier.

8. A pharmaceutical composition useful as an anti-arrythmic agent and comprised of at least one anti-arrythmic effective amount of the pyridine derivative of claim 2 and a pharmaceutically acceptable carrier.

9. A pharmaceutical composition useful as an anti-arrythmic agent and comprised of at least one anti-arrythmic effective amount of the pyridine derivative of claim 3 and a pharmaceutically acceptable carrier.

10. A pharmaceutical composition useful as an anti-arrythmic agent and comprised of at least one anti-arrythmic effective amount of the pyridine derivative of claim 4 and a pharmaceutically acceptable carrier.

11. A pharmaceutical composition useful as an anti-arrythmic agent and comprised of at least one anti-arrythmic effective amount of the pyridine derivative of claim 5 and a pharmaceutically acceptable carrier.

12. A pharmaceutical composition useful as an anti-arrythmic agent and comprised of at least one anti-arrythmic effective amount of the pyridine derivative of claim 6 and a pharmaceutically acceptable carrier.

13. A method of imparting anti-arrythmic activity to a subject, which comprises administering to said subject an anti-arrythmic effective amount of the pharmaceutical composition of claim 7.

14. The method of claim 13 wherein the pharmaceutical composition contains from about 1 to about 600 mg of said pyridine derivative.

15. The method of claim 14 wherein said pharmaceutical composition is administered in a daily dose of from about 1 to 200 mg.

16. The method of claim 14 wherein said pharmaceutical composition is administered in a daily dose of from about 100 to 600 mg.

* * * * *